United States Patent [19]
Butzer

[11] Patent Number: 5,483,346
[45] Date of Patent: Jan. 9, 1996

[54] POLARIZATION BASED OPTICAL SENSOR UTILIZING TOTAL INTERNAL REFLECTION

[76] Inventor: Dane C. Butzer, 1380 Harrison Pond Dr., New Albany, Ohio 43054

[21] Appl. No.: 225,888

[22] Filed: Apr. 11, 1994

[51] Int. Cl.⁶ .................................................. G01J 4/00
[52] U.S. Cl. .......................... 356/369; 356/239; 250/225; 318/483
[58] Field of Search .................. 356/369, 364, 356/370, 239, 128, 240, 338, 445, 133–137; 250/225, 902, 903, 227.17, 227.25, 573; 318/483, 444, DIG. 2; 385/12; 340/602; 73/29.01

[56] References Cited

U.S. PATENT DOCUMENTS

| | | | |
|---|---|---|---|
| Re. 33,064 | 9/1989 | Carter et al. | 356/414 |
| 2,359,787 | 10/1944 | Peters et al. | 250/227.25 |
| 2,977,842 | 4/1961 | Duke et al. | 88/14 |
| 3,451,740 | 6/1969 | Smith | 356/369 |
| 3,540,025 | 11/1970 | Levin et al. | 356/136 |
| 3,770,352 | 11/1973 | White | 356/133 |
| 3,985,447 | 10/1976 | Aspres | 356/369 |
| 4,221,962 | 9/1980 | Black et al. | 250/227 |
| 4,297,032 | 10/1981 | Temple | 356/239 |
| 4,355,271 | 10/1982 | Noack | 318/480 |
| 4,481,450 | 11/1984 | Watanabe et al. | 318/444 |
| 4,620,141 | 10/1986 | McCumber et al. | 318/483 |
| 4,652,745 | 3/1987 | Zanardelli | 250/227.25 |
| 4,669,875 | 6/1987 | Shiba et al. | 356/237 |
| 4,676,638 | 6/1987 | Yasuda | 356/136 |
| 4,924,084 | 5/1990 | Lask et al. | 250/227.25 |
| 4,994,682 | 2/1991 | Woodside | 250/577 |
| 5,015,931 | 5/1991 | Muller | 318/443 |
| 5,059,396 | 10/1991 | Opitz et al. | 422/82.11 |
| 5,094,517 | 3/1992 | Franke | 385/12 |
| 5,185,644 | 2/1993 | Schimoyama et al. | 356/369 |
| 5,323,637 | 6/1994 | Bendicks et al. | 318/483 |

FOREIGN PATENT DOCUMENTS

| | | | |
|---|---|---|---|
| 0144239 | 6/1988 | Japan | 356/137 |
| 2156970 | 10/1985 | United Kingdom | 356/432 |

OTHER PUBLICATIONS

A Highly Efficient Interconnect For Use With a Multistage Optical Switching Network With Orthogonally Polarized Data and Address Information by: Dane C. Butzer; 1994; pp. 1–5, 55–70

Disclosure Document #330165, An Optical Sensor For the Detection of Water Or Other Substances On Glass Or Other Transparent Materials, Dane Butzer 1993.

Disclosure Document #331957, An Improved Optical Sensor For the Detection of Water Or Other Substances On Glass or Other Transparent Materials, Dane Butzer, 1993.

*Primary Examiner*—Hoa Q. Pham

[57] ABSTRACT

A polarization based optical sensor for detecting the presence, composition, or both of substances (26) on a transparent material's (12) surface (14). A polarized-light source (18) introduces light (22) into the material (12). Within the material (12), the light (22) undergoes one or more total internal reflections (18, 20) whether or not the substance to be detected or analyzed (26) is present. The presence of the substance causes a shift in the polarization of the light (22). This shift is detected by a polarized-light detector (20) when the light (22) exits the material (14).

12 Claims, 2 Drawing Sheets

Prior Art

POLARIZATION BASED OPTICAL SENSOR UTILIZING TOTAL INTERNAL REFLECTION

BACKGROUND—FIELD OF INVENTION

This invention relates to the use of the polarization shift caused by the total internal reflection of light at the boundary of a transparent material to detect the presence, composition, or both, of substances on the material's surface.

BACKGROUND OF THE INVENTION

Light-based sensors exist which detect the presence or composition of substances on a material's surface. Some of these utilize the principle of the attenuation of internal reflection of light in the material caused by the presence of the substance to be detected. These include those described in U.S. Pat. No. 3,540,025 to Levin et al. (1970), U.S. Pat. No. 4,355,271 to Noack (1982), U.S. Pat. No. 4,620,141 to McCumber et al. (1986), U.S. Pat. No. 4,652,745 to Zandarelli (1987), and U.S. Pat. No. 5,015,931 to Muller (1991). In addition, many devices in the field of spectroscopy operate through the use of attenuated total internal reflection (ATR) plates. In all of these cases, the devices operate by introducing light into some material such that it undergoes one or more total internal reflections. This light then exits the material and strikes a detector of some sort. The amount of light reaching the detector is affected by the presence of a substance on the surface of the material when the substance changes the efficiency of one or more of the internal reflections. This change in efficiency occurs because of the different index of refraction of the substance compared to the surrounding medium (such as air).

U.S. Pat. No. 3,540,025 to Levin et al. (1970) is the first device found described in a patent which uses the principle of attenuated total internal reflection. This device is specifically designed to detect the presence of ice on the surface of some material. If no ice is present, a light beam undergoes total internal reflection at the surface. If ice is present, the difference in the index of refraction at the surface attenuates the internal reflection(s).

The devices described in the patents listed above also work on similar principles. The ice detector should perform its task admirably. However, neither it nor the other devices are suitable for detecting the presence of drops of water or other liquids on a surface in an uncontrolled environment or on a curved surface. For example, they would not work well for detecting water on the surface of a flat section of a windshield or across the entire surface of a curved windshield. These devices suffer from three main problems.

First, the devices in Levin et al. (first embodiment), Noack, and McCumber et al. detect substances only in some small area. In an uncontrolled environment, this area could become fouled with dirt, some sticky substance, or the such. Some of the devices, such as those in Levin et al. (second embodiment), Zandarelli, and Muller overcome this fault by using multiple internal reflections throughout the material. However, this solution introduces another problem.

With multiple internal reflections, it can be very difficult to accurately determine the amount of liquid or the such on a material's surface. This is because light can exit the material at one point only to re-enter it at another. When the light is attenuated through exiting a material at a drop of some liquid, it often travels nearly parallel to the material's surface. Thus, this light can easily re-enter the material if it strikes a second drop of liquid. In addition, ambient light traveling along the material's surface can also enter the material at these drops. One proposed solution to this problem is to use light stops to limit the direction that the light can take to reach the detector. This is ineffective since the light beams can easily re-enter the material in such a way that their direction is parallel, or nearly parallel, to the totally reflected light. The same is true for ambient light. This combination of circumstances makes it very difficult for a multiple reflection attenuation type sensor to accurately determine the amount of liquid or the such on a material's surface.

The third problem with the multiple internal reflection devices is that it is difficult, if not impossible, to introduce a light beam into a curved material such that it is always totally reflected in the "dry" cases, and not totally reflected in the "wet" cases.

Other patents which are generally related to optical sensing of substances include U.S. Pat. No. 2,977,842 to Duke et al. (1961), U.S. Pat. No. 4,221,962 to Black et al. (1980), U.S. Pat. No. 4,669,875 to Shiba et al. (1987), U.S. Pat. No. Re. 33,064 to Carter et al. (1989), U.S. Pat. No. 4,924,084 to Lask et al. (1990), U.S. Pat. No. 4,994,682 to Woodside (1991), U.S. Pat. No. 5,059,396 to Opitz et al. (1991), U.S. Pat. No. 5,094,517 to Franke (1992), and U.S. Pat. No. 5,185,644 to Shimoyama et al. (1993). None of these patents suggests an obvious means of overcoming the problems with the devices noted above. U.S. Pat. No. 4,669,875 to Shiba et al. is of note since it utilizes polarization considerations in the detection of foreign substances. However, it does not utilize total internal reflection, and operates on different principles than the current invention. U.S. Pat. No, 5,094,517 to Franke is also of note as it utilizes polarization considerations for the detection of liquids in vapor phase, $NH_3$, $NH_4OH$, and $N_2O_5$. However, it utilizes polyimide-imide or perfluorinated polyimide layers. These layers are not required by the current invention.

Finally, another related patent which utilizes polarization effects is U.S. Pat. No. 3,451,740 to Smith. The invention described therein is a magneto-optical switch based on polarization effects. It utilizes a magnetic film that is not present in the current invention.

SUMMARY OF THE INVENTION

There is disclosed an invention in a polarization based optical sensor utilizing total internal reflection comprising a polarized-light source, a polarized-light detector sensitive to a particular polarization of light, and a transparent material that is transparent to the polarized light. The polarized-light source is oriented so that the light it emits undergoes one or more substantially total internal reflection(s) within the transparent material and is detected by the polarized-light detector. The presence or composition of a substance or substances on the transparent material's surface causes a shift in the polarization of the light at the internal reflections. This results in a change in the polarization of the light striking the polarized-light detector, in turn resulting in a change in the output of the polarized-light detector.

There is also disclosed an invention in the polarization based optical sensor as described above wherein the polarized-light source comprises an arbitrary-light source and a source polarizer. The arbitrarily-polarized light from the arbitrary-light source passes through the source polarizer and is polarized.

There is also disclosed an invention in the polarization based optical sensor as described above wherein the polarized-light detector comprises an arbitrary-light detector sensitive to any arbitrary polarization of light, and a detector polarizer. The light is polarized by the detector polarizer before striking the arbitrary-light detector.

There is also disclosed an invention in the polarization based optical sensor as described above wherein the polarized-light source comprises an arbitrary-light source and a source polarizer, and the polarized-light detector comprises an arbitrary-light detector and a detector polarizer.

There is also disclosed an invention in the polarization based optical sensor as described above wherein the transparent material is a vehicle windshield.

There is also disclosed an invention in the polarization based optical sensor as described above wherein the transparent material is an ATR plate of the type typically used in spectroscopy.

There is also disclosed an invention in the polarization based optical sensor as described above wherein the polarized-light source is oriented such that the light is polarized so that the vector of the electric field for the polarization of the light lies neither completely parallel to nor completely perpendicular to the plane of incidence of the light for the internal reflection(s).

There is also disclosed an invention in the polarization based optical sensor as described above wherein the polarized-light detector is oriented such that it is sensitive to light polarized so that the vector of the electric field for the polarization of the light lies neither completely parallel to nor completely perpendicular to the plane of incidence of the light for the internal reflection(s).

There is also disclosed an invention in the polarization based optical sensor as described above wherein the polarized-light source is oriented such that the light is polarized so that the vector of the electric field for the polarization of the light lies neither completely parallel to nor completely perpendicular to the plane of incidence of the light for the internal reflection(s), and the polarized-light detector is oriented such that it is sensitive to light polarized such that the vector of the electric field for the polarization of the light lies neither completely parallel to nor completely perpendicular to the plane of incidence of the light for the internal reflection(s).

There is also disclosed an invention in the polarization based optical sensor as described above further comprising a source coupler between the polarized-light source and the transparent material for coupling the light from the polarized-light source into the transparent material.

There is also disclosed an invention in the polarization based optical sensor as described above wherein the source coupler is a prism.

There is also disclosed an invention in the polarization based optical sensor as described above further comprising a detector coupler between the transparent material and the polarized-light detector for coupling the light from the transparent material into the polarized-light detector.

There is also disclosed an invention in the polarization based optical sensor as described above wherein the detector coupler is a prism.

There is also disclosed an invention in the polarization based optical sensor as described above further comprising a source coupler between the polarized-light source and the transparent material for coupling the light from the polarized-light source into the transparent material, and a detector coupler between the transparent material and the polarized-light detector for coupling the light from the transparent material into the polarized-light detector.

There is also disclosed an invention in the polarization based optical sensor as described above further comprising one or more light stop(s) situated before the polarized-light detector for restricting the light entering the polarized-light detector.

There is also disclosed an invention in the polarization based optical sensor as described above wherein the polarized-light detector further comprises an arbitrary-light detector and a detector polarizer, further comprising one or more light stop(s) situated before the arbitrary-light detector for restricting the light entering the arbitrary-light detector.

There is also disclosed an invention in the polarization based optical sensor as described above wherein there are multiple polarized-light sources.

There is also disclosed an invention in the polarization based optical sensor as described above wherein there are multiple polarized-light detectors.

There is also disclosed an invention in the polarization based optical sensor as described above wherein there are multiple polarized-light sources and multiple polarized-light detectors.

Figure 3:
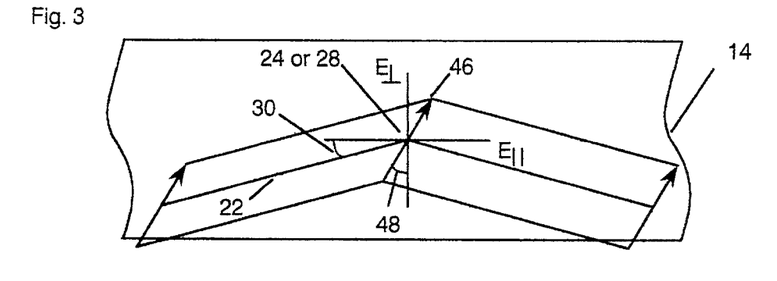
FIG. 3 discloses a sensor of this invention in use.

The objects and advantages of the present invention are:

(1) provide a means for detecting the presence or composition of a substance on some material through the use of polarization effects and total internal reflection;

(2) provide such a detection means that will work in an uncontrolled environment;

(3) provide such a detection means that will work across part or all of a curved surface such as a windshield;

(4) provide such a detection means that does not suffer from the problem shown in FIG. 3 and described above;

(5) and provide such a detection means that is totally unaffected by the presence of ambient light.

Further features and advantages of the invention will appear from a reading of the detailed description which follows, which is given by way of example only and with reference to the accompanying drawings.

REFERENCE NUMERALS IN DRAWINGS

| REFERENCE NUMERALS IN DRAWINGS | |
|---|---|
| 10 polarization based optical sensor utilizing total internal reflection | 12 transparent material |
| 14 material boundary | 16 surrounding medium |
| 18 polarized-light source | 20 polarized-light detector |
| 22 light | 24 total internal reflection |
| 26 substance to be detected or analyzed | 28 total internal reflection |
| 30 angle of incidence | 32 transparent material |
| 34 material boundary | 36 surrounding medium |
| 38 first drop of liquid | 40 second drop of liquid |
| 42 first light beam | 44 second light beam |
| 46 initial vector of electric field polarization | 48 angle of polarization |
| 50 arbitrary-light source | 52 source polarizer |
| 54 detector polarizer | 56 arbitrary-light detector |
| 58 source coupling prism | 60 detector coupling prism |
| 62 light stops | |

DETAILED DESCRIPTION OF THE DRAWING FIGURES

Figure 1:
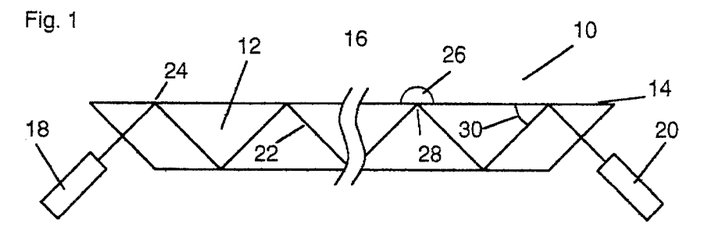
FIG. 1 discloses a possible embodiment of the polarization based optical sensor utilizing total internal reflection.

Having reference to the drawings, attention is first directed to FIG. 1 which discloses a typical embodiment of the polarization based optical sensor, shown generally depicted by the numeral 10. A polarized-light source 18 shines light 22 into a transparent material 12. Some possible examples of transparent material 12 are glass, clear plastic, lexan, or alumina (the last for IR light). Light 22 undergoes total internal reflection 24 at a material boundary 14 where a surrounding medium 16 is present. Light 22 also undergoes total internal reflection 28 at medium boundary 14 where a substance to be detected or analyzed 26 is present. Some possible examples of substance to be detected or analyzed 26 are water, windshield wiper fluid, or test material for spectroscopy. Light 22 exits transparent material 12 and is detected by a polarized-light detector 20.

Figure 2:
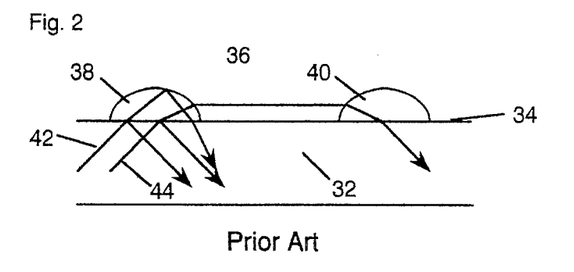
FIG. 2 discloses a sensor problem of the type described in the prior art.

FIG. 2 illustrates a major flaw with the sensors described in the prior art which rely on attenuation of multiple total internal reflections. A first light beam 42 strikes a material boundary 34 of a transparent material 32 where a first drop of liquid 38 is present. Part of first light beam 42 passes into first drop of liquid 38, where it is reflected off of the boundary of the liquid with surrounding medium 36. This causes it to re-enter transparent material 32. A second light beam 44 also strikes material boundary 34 at first drop of liquid 38. Part of second light beam 44 passes into first drop of liquid 38, where it is deflected by the boundary of the liquid with surrounding medium 36 into a second drop of liquid 40. Second light beam 44 is then deflected back into transparent material 32 by second drop of liquid 40. In both of these cases, which were commonly observed while testing a multiple internal reflection attenuation type of sensor, the drops of liquid are not properly detected since the light is not predictably attenuated.

FIG. 3 shows the mechanism of the polarization shift for the polarization based optical sensor of this invention. Light 22 undergoes total internal reflection 24 or 28 at material boundary 14. The angle of incidence 30 of the light is such that the light undergoes total internal reflection regardless of whether or not a substance to be detected or analyzed 26 (not shown) is present. The initial vector of electric field polarization 46 for the light is in neither the $E_{\parallel}$ nor the $E_{\perp}$ directions. In other words, an angle of polarization 48 between initial vector of electric field polarization 46 and $E_{\perp}$ exists which is not 0° and in not a multiple of 90°. Note that the polarization of light 22 both before and after the reflection need not be linear as shown. In fact, the polarization after the reflection is most likely elliptical regardless of the polarization before the reflection. However, it is shown here as linear for cosmetic reasons.

Figure 4:
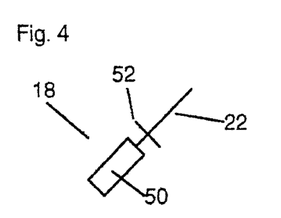
FIG. 4 discloses a possible composition of the polarized-light source for this invention.

FIG. 4 shows a possible composition of polarized-light source 18. An arbitrary-light source 50, whose light may or may not be polarized, shines through a source polarizer 52.

Figure 5:
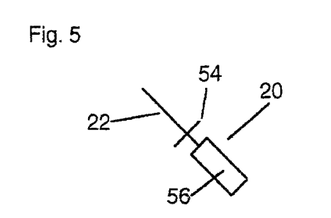
FIG. 5 discloses a possible composition of the polarized-light detector for this invention.

FIG. 5 shows a possible composition of polarized-light detector 20. A detector polarizer 54 polarizes light 22 before it reaches an arbitrary-light detector, which may be sensitive to unpolarized light or some specific polarization of light.

Figures 6, 7, 8, 9:
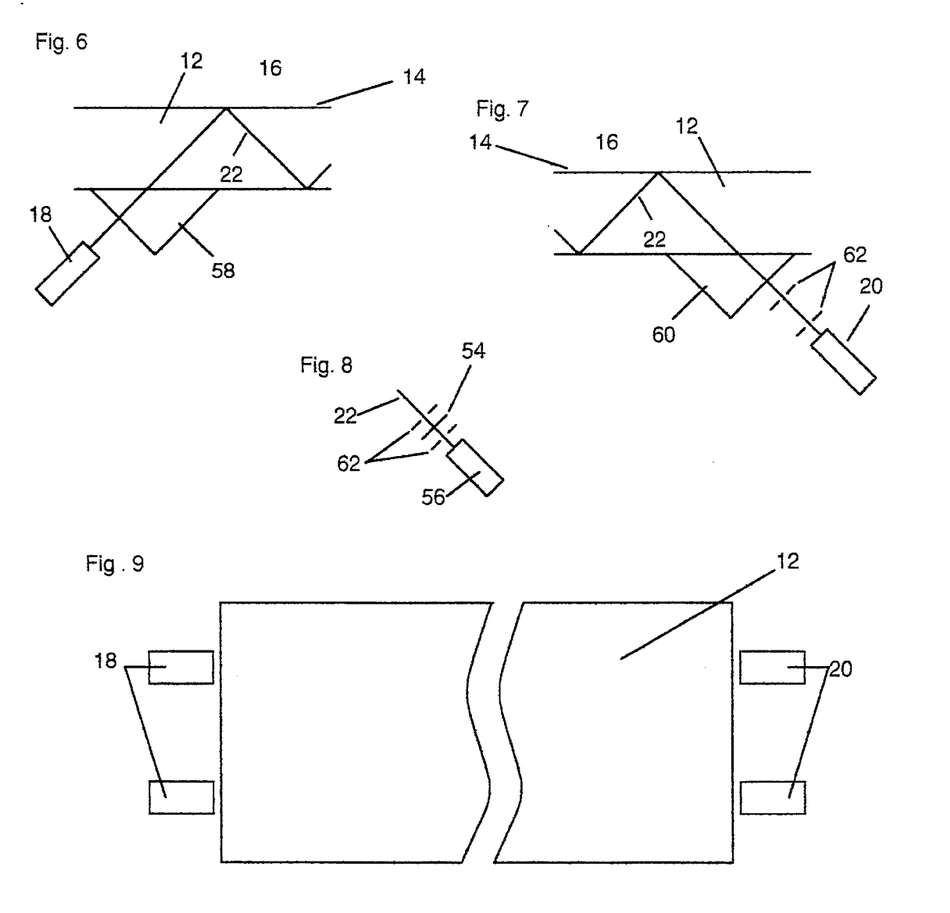
FIG. 6 discloses an alternate method for coupling the light from the polarized-light source into the transparent material for this invention.
FIG. 7 discloses an alternate method for coupling the light from the transparent material into the polarized-light detector, and the use of light stops to restrict the light striking the polarized-light detector for this invention.
FIG. 8 discloses another possible placement for light stops for this invention.
FIG. 9 discloses a configuration of the polarization based optical sensor utilizing total internal reflection incorporating multiple polarized-light sources and multiple polarized-light detectors.

FIG. 6 shows an alternate method for coupling light 22 into transparent material 12. Light 22 from polarized-light source 18 enters a source coupling prism 58. Light 22 then passes into transparent material 12.

FIG. 7 shows an alternate method for coupling light 22 out of transparent material 12. In addition, the use of light stops 62 to limit the angle of the light that reaches polarized-light detector 20 is shown. Light beam 22 exits transparent material 12 though detector coupling prism 60. Two light stops 62 are placed before polarized-light detector 20. Note that any number of light stops can be used. In the case of a polarized-light detector 20 that consists of arbitrary-light detector 56 and detector polarizer 54, one or more light stop(s) can be placed before, after, or before and after detector polarizer 54.

FIG. 8 shows a possible configuration for positioning light stops 62 in the case of a polarized-light detector 20 that consists of arbitrary-light source 56 and detector polarizer 54.

FIG. 9 shows a possible configuration for using multiple polarized-light sources 18 and polarized-light detectors 20 to increase the detection area. More sources and detectors in many other configurations are also possible.

DESCRIPTION OF THE INVENTION

Operation:

The operation of the polarization based optical sensor is quite different from that of the other total internal reflection type sensors. Unlike previous sensors, a light 22 within a transparent material 12 undergoes total internal reflection at a material boundary 14 regardless of whether or not a substance to be detected or analyzed 26 is present. In other words, an angle of incidence 30 is both greater than the critical angle for reflections at the boundary between transparent material 12 and surrounding medium 16 and greater than the critical angle for reflections at the boundary between transparent material 12 and substance to be detected or analyzed 26. A possible version of this arrangement is shown in FIG. 1. Also, light 22 is polarized before it enters material 12. This provides the means for detecting some substance on the material.

As a light undergoes total internal reflection at medium boundary 14, a phase shift is introduced between the parts of the fields in the $E_{\parallel}$ and $E_{\perp}$ directions. $E_{\parallel}$ lies in the plane of incidence of the light, and $E_{\perp}$ lies perpendicular to the plane of incidence. FIG. 3 shows the orientation of $E_{\parallel}$ and $E_{\perp}$ at material boundary 14 for the optical sensor. The phase shift, say $\delta$, is a function of the materials at the boundary and of the angle of incidence 30 of the light. The equation for $\delta$ is:

$$\delta = 2\arctan\left( \frac{(n_1/n_2)[(n_1/n_2)^2 - 1]\sin^2(\theta)}{[(n_1/n_2)^2 - 1]\cos(\theta)[(n_1/n_2)^2\sin^2(\theta) - 1]^{1/2}} \right)$$

where $n_1$ is the index of refraction of transparent material 12 and $n_2$ is the index of refraction of the substance on the other side of the boundary. Therefore, if substance to be detected or analyzed 26 is present on the other side, the phase shift has one value. If the substance is not present, the phase shift has another value.

Now, directly measuring the phase shift between the two polarizations would be extremely difficult. However, if light 22 is polarized such that an initial vector of electric field polarization 46 is neither completely in the $E_\parallel$ direction nor completely in the $E_\perp$ direction, the change in the phase shift can be easily detected. A possible alignment of the polarizations is shown in FIG. 3.

Letting $E_O$ be the field strength of the part of light 22 in the direction of initial vector of electric field polarization 46 before reflection, letting $E_C$ be the field strength of the part of light 22 perpendicular to initial vector of electric field polarization 46 before reflection, and letting $\phi$ be the angle of polarization 48 between the directions of $E_O$ and $E_\perp$, expressions for the fields after total internal reflection are:

$E_O' = (E_O \cos(\phi) e^{i\delta} + E_C \sin(\phi) e^{i\delta}) \cos(\phi) + (E_O (-\sin(\phi)) + E_C \cos(\phi))(-\sin(\phi))$ $E_C' = (E_O \cos(\phi) e^{i\delta} + E_C \sin(\phi) e^{i\delta}) \sin(\phi) + (E_O (-\sin(\phi)) + E_C \cos(\phi)) \cos(\phi)$ Here, the primes indicate the fields after reflection.

There are three key points to note about the above relations. First, there is clearly an exchange of energy between the $E_O$ and the $E_C$ polarizations. Second, this exchange is dependent on $\delta$, which is in turn dependent on the indices of refraction at the reflection. This provides the means for detecting the presence of substance to be detected or analyzed 26. Third, the relation between $\delta$ and the exchange of energy is not linear.

Since these relations are non-linear, a computer simulation is useful in analyzing them. Through such a simulation, another important point becomes apparent. When the equations are used to model multiple successive reflections, a change in $\delta$ at one reflection always affects the final values for the fields after all reflections. In addition, the order or placement of reflections with different $\delta$s does not matter. For example, if eight reflections are modeled and five of them have a $\delta$ corresponding to reflections with air while the other three have one corresponding to reflections with water, the order of the reflections could be {air, air, air, air, air, water, water, water}, or {water, air, water, air, water, air, air, air}, or any other order. The final fields strengths are all the same in each case.

The basis for the operation of the polarization based sensor, then, is to introduce light 22 from polarized-light source 18 into transparent material 12 in such a way that:

1) light 22 undergoes total internal reflection at material boundary 14, regardless of whether surrounding medium 16 or substance to be detected or analyzed 26 is on the other side, and 2) light 22 has initial vector of electric field polarization 46 oriented such that angle of polarization 48 between the initial vector and $E_\perp$ is nonzero and not a multiple of 90°. Polarized-light source 18 is oriented to achieve the second condition.

After the light undergoes one or more total internal reflections, it exits transparent material 12. In order to detect the exchange of energy between the $E_O$ and $E_C$ polarizations, light 22 is measured with polarized-light detector 20. The actual form of the output of polarized-light detector 20 is immaterial, and is not shown. However, the output is typically electrical in nature with a change in the output voltage, amperage, capacitance, inductance, and/or resistance indicating a change in the strength the appropriate polarization of the light reaching the detector.

If a light stop or stops 62 are used, the light reaching the detectors is limited to that traveling in the correct direction. Since light traveling in this direction undergoes total internal reflection at material boundary 14 in all cases, it is impossible for ambient light to enter transparent material 12 in such a way that it passes the light stop(s).

The strength of the light reaching polarized-light detector 20 could be used to directly note how many of the total internal reflections occur at boundaries with surrounding medium 14 and how many occur at boundaries with substance to be analyzed or detected 26. This could be accomplished by a table look-up of all possible values. An alternate approach exits which is useful when detecting a change in the presence of a substance. With this approach, the output of polarized-light detector 20 is monitored for changes. Whenever the presence of the substance to be analyzed or detected 26 changes, the output of polarized-light detector 20 changes.

Variations:

There exist numerous variations on the polarization based optical sensor. Some of these are described below. This is not to be taken as an exhaustive iteration of the possible variations. Rather, it simply provides examples for the application and utilization of the invention.

There exist many light sources which inherently generate polarized light. Such a source would work for polarized-light source 18. This type of light source can also be constructed from an arbitrary-light source 50 and a source polarizer 52. An arbitrary-light source is a light source that generates arbitrarily-polarized light. In other words, any type of light source qualifies as an arbitrary-light source. The light from the arbitrary-light source may be polarized in some specific direction or manner, or randomly polarized (unpolarized). A possible arrangement of this construction is shown in FIG. 4.

Similarly, there are light detectors which are inherently sensitive to only certain polarizations of light. Such a detector would work for polarized-light detector 20. This type of light detector can also be constructed from a detector polarizer 54 and an arbitrary-light detector 56. An arbitrary-light detector is a light detector that is sensitive to arbitrarily-polarized light. In other words, any type of light detector qualifies as an arbitrary-light detector. The arbitrary-light detector may be sensitive to some specific polarization of light to or randomly polarized (unpolarized) light. A possible arrangement for this construction is shown in FIG. 5. Note that many items can serve as the polarizers in these cases. Some examples include but are not limited to: discrete polarizers, gratings etched onto the transparent material, and even the boundary of the transparent material at the entry and exit points for the light. In the last case, the light is polarized by having it enter or exit the glass at Brewster's angle.

Possible light sources (both polarized and arbitrary) include but are not limited to: LED's, laser diodes, any of the numerous other types of lasers, incandescent light bulbs, fluorescent light sources, X-ray sources, and chemical light sources. The LED and laser sources are particularly good candidates, but not the only ones, for producing inherently polarized light.

Possible light detectors (both polarized and arbitrary) include but are not limited to: photo-voltaic cells, photo transistors, photo resistors, and film. Photo transistors are particularly good candidates, but not the only ones, for detectors that are inherently sensitive to only certain polarizations of light.

Depending on the nature of the light source, there are many materials which can be used as transparent material 12. The sole requirement for these materials is that they must be transparent to the light from polarized-light source 20. For example, if light 22 from the source is visible light, then clear glass, plastic, lexan, or the such can be used. If the light 22 is infrared (IR), then materials that are transparent to IR to visible light, can be necessarily transparent to visible light can be used. An example of such a material is alumina ($Al_2O_3$). Note that light in this case refers to any type of applicable electromagnetic radiation.

In addition, there are many possible methods for coupling light 22 into an out of transparent material 12. The edges of the material could be beveled as in FIG. 1. Alternatively, a source coupler and/or a detector coupler could be used. FIG. 6 and 7 show possible arrangements of this type where the couplers are prisms.

As mentioned earlier, light stops can be used to restrict light 22 reaching polarized-light detector 20 to that traveling in the desired direction. One or more light stops 62 can be used. In the case that polarized-light detector 20 comprises arbitrary-light detector 56 and detector polarizer 54, one or more light stops can be placed before, after, or before and after detector polarizer 54. One possible arrangement of this is shown in FIG. 8.

Finally, while the above discussion is focused on a single light source/single light detector type of sensor, there is no reason that a multiple light source/multiple light detector scheme could not be implemented based on the same principles. A possible arrangement for this is shown in FIG. 9. In addition, many of the modulation schemes described in the prior art are equally applicable for this sensor. Refer to Noack (1982) and Muller (1991) for examples of such schemes.

Application Examples:

The polarization based optical sensor has at least two applications: as a rain sensor for a vehicle windshield and as a spectroscopy tool.

The second approach described above, where the output of the polarized-light detector is monitored for changes, is ideal for the rain sensor application. Used this way, the polarization based optical sensor is far superior to the attenuation type of sensors described in the prior art.

For a rain sensor, the polarized light enters and exits the windshield at an edge using an arrangement such as in FIG. 1, or at some point on the surface using an arrangement as in FIG. 6 and 7. The light undergoes several total internal reflections across the windshield. Note that with a typical windshield, the number of reflections can be on the order of 100. This provides around 100 sensing points. The angle of incidence of the light at each reflection is greater than the critical angle for a reflection at a boundary between the windshield material and air, water, ice, windshield wiper fluid, etc.

After all of the reflections, the light exits the glass. Again, the light can exit through the side of the glass (FIG. 1) or through the surface (FIG. 7). Light stops are used to restrict the light striking the detector to the correct direction. This eliminates ambient light effects. Any rain, mud, etc. striking the windshield causes a change in the phase of the polarizations of the light as described above. This in turn causes a change in the exchange of energy between the $E_O$ and $E_C$ polarizations which is detected by the polarized-light detector.

The light detector should be monitored for changes relatively rapidly. Thus, each event that causes a change in the phase shift, for example a rain drop striking the windshield at a sensing point, can be noted even in a rapidly changing environment such as a storm. Once enough changes are noted, some device can activate the car's windshield wipers. A more sophisticated system can use the amount of change in the light reaching the polarized-light detector to compute the exact change in the exchange of energy each time something causes a phase shift. From this, some specialized action could be initiated. For example, if mud or insects are detected, the control device could also activate the washer fluid mechanism.

The main advantages or this approach over ones using the attenuated reflection types of sensors are:

1) As total internal reflection occurs in both the "wet" and "dry" type of reflections, the problems illustrated in FIG. 3 and noted in the description of prior art can not occur.
2) Since the light stops limit the light reaching the detector to that which always undergoes total internal reflection across the windshield, it is impossible for any amount of ambient light to strike the light detector. Thus, the polarization based sensor is totally immune to the effects of ambient light.
3) This sensor will work just as well across a curved piece of windshield as a flat one. The angle of incidence only has to be greater than the critical angles for boundaries between the windshield material and air, water, ice, etc. This should be easy to achieve. In other words, instead of having to align the light so that it falls within some range, as is necessary with the attenuation type sensors (greater than the critical angle for reflections at air and less than the critical angle for the reflections at water), there is only a lower limit to the critical angle with the polarization based sensor.
4) As total internal reflection occurs in both the "wet" and "dry" types of reflections, the amount of light present at all reflections is the same. Only the relative powers of the light in the $E_O$ and $E_C$ polarizations changes. Therefore, the sensor is equally sensitive at all reflections across the windshield.
5) If some dirt, ice, or other material becomes affixed to the windshield at a detection point, it causes a static change in the phase shift (and thus detected light). Since the change is static, it does not interfere in any way with the detection of rain, mud, etc. at the other reflection points. In addition, if there is a change in the dirt or ice (i.e. it melts or becomes wet), this change is detected.

For the spectroscopy application, very precise measurements of the output of the polarized-light detector can be taken. The precise phase shift can be calculated from these measurements. This shift would give some indication as to the composition of the substance. The main advantage of this approach over ATR type spectroscopy is that only an exponentially decaying evanescent electromagnetic field enters the test substance. Thus, this sensor can be useful with light sensitive test substances.

SUMMARY, RAMIFICATIONS, AND SCOPE

The polarization based sensor described above clearly has advantages over other types of sensors with similar applications. These result from the fact that the light in the transparent material (such as a vehicle windshield or an ATR plate) always undergoes total internal reflection regardless of the presence of the substance to be detected or analyzed. Thus, the light stays in the material, providing uniform sensitivity across the entire detection area. Also, many problems associated with stray beams and ambient light are eliminated. The specific advantages of this sensor for two applications, as a rain detector for a windshield and as a spectroscopy tool, have been detailed.

The use of polarization effects for this type of internal reflection sensor is novel. The unobviousness is emphasized by the fact that no other internal reflection type sensor uses light beams that undergo total internal reflections regardless of whether or not the substance to be detected or analyzed is present.

Finally, there are many orderings and combinations of light source(s), light detector(s), polarizer(s), prism(s), light stop(s), etc. that achieve the desired effects. Therefore, the scope of this invention should be determined by the appended claims and their legal equivalents rather than the examples given above.

What is claimed is:

1. A polarization based optical sensor utilizing total internal reflection for detecting substances and changes in said substances on a transparent material comprising at least one polarized-light source that generates a polarized light, at least one polarized-light detector that is sensitive to a particular polarization of light, and said transparent material that is transparent to said polarized light;

said polarized-light source oriented so that said polarized light produced thereby enters said transparent material, undergoes a number of substantially-total-internal reflections within said transparent material by striking a boundary of said transparent material at an angle of incidence greater than both a critical angle for a surrounding medium and a critical angle for said substances, exits said transparent material, and strikes said polarized-light detector;

said polarized-light source also oriented so that said polarized light produced thereby has an original-electric field consisting of a parallel-electric field parallel to a plane of incidence of said substantially-total-internal reflections and a perpendicular-electric field perpendicular to said plane of incidence of said substantially-total-internal reflections;

said polarized light having a phase shift between said parallel-electric field and said perpendicular-electric field;

said phase shift dependent upon an index of refraction of said substances and said surrounding medium at said substantially-total-internal reflections, a change in said substances causing a corresponding change in said index of refraction, in turn causing a resulting change in said phase shift;

said resulting change in said phase shift causing a transfer of energy between said original-electric field and an electric field perpendicular to said original-electric field;

said polarized-light detector oriented so that said transfer of energy causes a measurable change in an output of said polarized-light detector;

whereby said substances and changes in said substances are detected.

2. The polarization based optical sensor as recited in claim 1 wherein said number of said substantially-total-internal reflections is one.

3. The polarization based optical sensor as recited in claim 1 wherein said number of said substantially-total-internal reflections is greater than one.

4. The polarization based optical sensor as recited in claim 1 wherein said transparent material is a vehicle windshield.

5. The polarization based optical sensor as recited in claim 1 wherein said transparent material is selected from the group consisting of glass, plastic, and alumina.

6. The polarization based optical sensor as recited in claim 1 wherein said polarized-light source comprises an arbitrary-light source that produces arbitrarily-polarized light, and a source polarizer; said arbitrarily-polarized light from said arbitrary-light source passing through said source polarizer.

7. The polarization based optical sensor as recited in claim 1 wherein said polarized-light detector comprises an arbitrary-light detector sensitive to arbitrarily-polarized light, and a detector polarizer; said polarized light passing through said detector polarizer before striking said arbitrary-light detector.

8. A method for detecting substances and changes in said substances on a transparent material using at least one polarized-light source and at least one polarized-light detector comprising the steps of:

shining a polarized light from said polarized-light source into said transparent material such that said polarized light undergoes a number of substantially-total-internal reflections within said transparent material by striking a boundary of said transparent material at an angle of incidence greater than both a critical angle for a surrounding medium and a critical angle for said substances;

propagating said polarized light through said transparent material with an original-electric field consisting of a parallel-electric field parallel to a plane of incidence of said substantially-total-internal reflections and a perpendicular-electric field perpendicular to said plane of incidence of said substantially-total-internal reflections;

changing a phase shift between said parallel-electric field and said perpendicular-electric field by changing said substances and thus changing an index of refraction of said substances at said substantially-total-internal reflections, a change in said phase shift causing a transfer of energy between said original-electric field and an electric field perpendicular to said original-electric field; and detecting said transfer of energy with said polarized-light detector after said polarized light exits said transparent material.

9. The method for detecting substances on a transparent material as recited in claim 8 wherein said number of said substantially-total-internal reflections is one.

10. The method for detecting substances on a transparent material as recited in claim 8 wherein said number of said substantially-total-internal reflections is greater than one.

11. The method for detecting substances on a transparent material as recited in claim 8 wherein said transparent material is a vehicle windshield.

12. The method for detecting substances on a transparent material as recited in claim 8 wherein said transparent material is selected from the group consisting of glass, plastic, and alumina.

* * * * *

UNITED STATES PATENT AND TRADEMARK OFFICE
CERTIFICATE OF CORRECTION

PATENT NO. : 5,483,346

Page 1 of 3

DATED : January 9, 1996

INVENTOR(S) : Dane C. Butzer

It is certified that error appears in the above-identified patent and that said Letters Patent is hereby corrected as shown below:

The title page, showing illustrative figures, should be deleted and substitute therefor the attached title page.

Delete FIGS. 1 and 3 and substitute FIGS 1 and 3 as shown on the attached page.

Column 2, line 13, change "is difficult" to "--may be difficult--."

Column 7, lines 18 to 22, change "Letting $E_O$ be the field strength of the part of light 22 in the direction of initial vector of electric field polarization 46 before reflection, letting $E_C$ be the field strength of the part of light 22 perpendicular to initial vector of electric field polarization 46 before reflection," to "--Letting $E_O$ be the field strength in the direction of initial vector of electric field polarization 46 of light 22 before reflection, letting $E_C$ be the field strength perpendicular to initial vector of electric field polarization 46 of light 22 before reflection,--."

Signed and Sealed this

Fourth Day of June, 1996

Attest:

BRUCE LEHMAN

*Attesting Officer*   *Commissioner of Patents and Trademarks*

United States Patent [19]

Butzer

[11] Patent Number: 5,483,346
[45] Date of Patent: Jan. 9, 1996

[54] POLARIZATION BASED OPTICAL SENSOR UTILIZING TOTAL INTERNAL REFLECTION

[76] Inventor: Dane C. Butzer, 1380 Harrison Pond Dr., New Albany, Ohio 43054

[21] Appl. No.: 225,888

[22] Filed: Apr. 11, 1994

[51] Int. Cl.⁶ .................................................. G01J 4/00
[52] U.S. Cl. .................. 356/369; 356/239; 250/225; 318/483
[58] Field of Search .................. 356/369, 364, 356/370, 239, 128, 240, 338, 445, 133–137; 250/225, 902, 903, 227.17, 227.25, 573; 318/483, 444, DIG. 2; 385/12; 340/602; 73/29.01

[56] References Cited

U.S. PATENT DOCUMENTS

| Re. 33,064 | 9/1989 | Carter et al. | 356/414 |
|---|---|---|---|
| 2,359,787 | 10/1944 | Peters et al. | 250/227.25 |
| 2,977,842 | 4/1961 | Duke et al. | 88/14 |
| 3,451,740 | 6/1969 | Smith | 356/369 |
| 3,540,025 | 11/1970 | Levin et al. | 356/136 |
| 3,770,352 | 11/1973 | White | 356/133 |
| 3,985,447 | 10/1976 | Aspres | 356/369 |
| 4,221,962 | 9/1980 | Black et al. | 250/227 |
| 4,297,032 | 10/1981 | Temple | 356/239 |
| 4,355,271 | 10/1982 | Noack | 318/480 |
| 4,481,450 | 11/1984 | Watanabe et al. | 318/444 |
| 4,620,141 | 10/1986 | McCumber et al. | 318/483 |
| 4,652,745 | 3/1987 | Zanardelli | 250/227.25 |
| 4,669,875 | 6/1987 | Shiba et al. | 356/237 |
| 4,676,638 | 6/1987 | Yasuda | 356/136 |
| 4,924,084 | 5/1990 | Lask et al. | 250/227.25 |
| 4,994,682 | 2/1991 | Woodside | 250/577 |
| 5,015,931 | 5/1991 | Muller | 318/443 |
| 5,059,396 | 10/1991 | Opitz et al. | 422/82.11 |
| 5,094,517 | 3/1992 | Franke | 385/12 |
| 5,185,644 | 2/1993 | Schimoyama et al. | 356/369 |
| 5,323,637 | 6/1994 | Bendicks et al. | 318/483 |

FOREIGN PATENT DOCUMENTS

| 0144239 | 6/1988 | Japan | 356/137 |
|---|---|---|---|
| 2156970 | 10/1985 | United Kingdom | 356/432 |

OTHER PUBLICATIONS

A Highly Efficient Interconnect For Use With a Multistage Optical Switching Network With Orthogonally Polarized Data and Address Information by: Dane C. Butzer: 1994; pp. 1–5, 55–70
Disclosure Document #330165, An Optical Sensor For the Detection of Water Or Other Substances On Glass Or Other Transparent Materials, Dane Butzer 1993.
Disclosure Document #331957, An Improved Optical Sensor For the Detection of Water Or Other Substances On Glass or Other Transparent Materials, Dane Butzer, 1993.

*Primary Examiner*—Hoa Q. Pham

[57] ABSTRACT

A polarization based optical sensor for detecting the presence, composition, or both of substances (26) on a transparent material's (12) surface (14). A polarized-light source (18) introduces light (22) into the material (12). Within the material (12), the light (22) undergoes one or more total internal reflections (18, 20) whether or not the substance to be detected or analyzed (26) is present. The presence of the substance causes a shift in the polarization of the light (22). This shift is detected by a polarized-light detector (20) when the light (22) exits the material (14).

12 Claims, 2 Drawing Sheets

Fig. 1

Fig. 3